United States Patent [19]
Singh et al.

[11] Patent Number: 5,635,089
[45] Date of Patent: *Jun. 3, 1997

[54] CERAMIC, METAL AND COMPOSITE MATERIALS HAVING INCREASED SURFACE AREA

[75] Inventors: Rajiv K. Singh; Brij M. Moudgil, both of Gainesville, Fla.; Sanjay Behl, Macon, Ga.; Deepika Bhattacharya, Gainesville, Fla.

[73] Assignee: University of Florida, Gainesville, Fla.

[*] Notice: The term of this patent shall not extend beyond the expiration date of Pat. No. 5,473,138.

[21] Appl. No.: 526,633

[22] Filed: Sep. 11, 1995

Related U.S. Application Data

[62] Division of Ser. No. 91,220, Jul. 13, 1993, Pat. No. 5,473,138.

[51] Int. Cl.$^6$ .................................................. B23K 26/00
[52] U.S. Cl. ...................... 219/121.69; 219/121.66; 219/121.68
[58] Field of Search .................. 219/121.61, 121.66, 219/121.68, 121.69, 121.72, 121.73; 428/156

[56] References Cited

U.S. PATENT DOCUMENTS

| | | | |
|---|---|---|---|
| 4,912,298 | 3/1990 | Daniels et al. | 219/121.69 |
| 4,972,061 | 11/1990 | Duley et al. | 219/121.66 |
| 5,175,043 | 12/1992 | Yabe et al. | 428/156 |
| 5,246,530 | 9/1993 | Bugle et al. | 156/643 |
| 5,473,138 | 12/1995 | Singh et al. | 219/121.69 |

Primary Examiner—Tu B. Hoang
Attorney, Agent, or Firm—Thomas C. Saitta

[57] ABSTRACT

A method for increasing the surface area and roughness of metals, ceramics and composites on a micro-scale, and the surfaces themselves, is disclosed whereby a laser beam having a radiation wavelength of from UV to infrared is pulsed onto the surface of the material. The energy density of the radiation is between 0.01 to 15 J/cm$^2$ and at least 50 pulses of radiation having duration of from 1 picosecond to 1 millisecond are used on each area. The surface structures formed are semi-periodic and are from ¼ to several hundred microns in magnitude.

12 Claims, 7 Drawing Sheets

CERAMIC, METAL AND COMPOSITE MATERIALS HAVING INCREASED SURFACE AREA

This application is a divisional of application Ser. No. 08/091,220, filed Jul. 13,1993, now U.S. Pat. No. 5,473,138, issued Dec. 5, 1995.

BACKGROUND OF THE INVENTION

This invention generally relates to a novel method for increasing the surface area of metals, ceramics, and composites by creating laser induced micro-rough structures on the surface of the material. More particularly, the invention relates to the use of multiple, relatively unfocused, laser pulses to dramatically increase surface roughness by creating surface morphological structures on a scale measurable in microns. The invention also relates to the modified metal, ceramic and ceramic composite surfaces produced by this method.

In many applications for metals, ceramics and composites (ceramic-ceramic, ceramic-metal, metal-metal, ceramic-polymer and metal-polymer), maximizing the true surface area of the material is desirable. Without altering dimensions, this maximization is accomplished by roughening the surface, since a planar surface will have considerably less true surface area than a non-planar surface having, for example, numerous peaks and valleys. Conventional techniques for roughening ceramic and ceramic composite surfaces, especially those attempting to affect the surface on a micro scale, are not effective. Because of the hardness of ceramic material, machining, polishing, grinding or sand blasting the surface has does little to increase surface roughness, and much care must be taken during such processing due to the inherent brittleness of many ceramics. Chemical and thermal etching likewise produce little increase in surface roughness. These processes mainly affect grain boundaries and have little effect within the grains themselves. Increasing the porosity of the ceramic during initial processing can increase true surface area, but the increase in porosity is accompanied by a decrease in strength of the final ceramic. Maximizing surface area or roughness on metal surfaces on a micro scale is also difficult, since melt flow characteristics often affect the final morphology.

Examples of applications where maximum surface area of a ceramic or metal material is desirable include ceramic catalysts and catalyst supports, bio-ceramic bone and dental implants, battery electrodes, structural composite materials where bonding strength is crucial, heat exchange and transfer ceramics, sensors, anti-reflective ceramics, particle filtration, fuel cells and applications where improved adhesion is required.

A novel and unique method has been developed whereby the inherent surface area of metals, ceramics and composites can be increased up to two orders of magnitude using multiple laser pulses. The method is independent of initial processing and is performed on the material surfaces after production. The method affects only the outermost surface of the materials to a depth of up to 200 microns, or as little as ¼ microns. Surface roughness and area is increased by the formation of periodic or semi-periodic micro-scale morphological structures in the nature of cones, peaks or columns having thicknesses of from ¼ to 100 microns and heights of from ¼ to 200 microns, with corresponding valleys or grooves with widths of from ¼ to 300 microns. The structures can be oriented in particular directions and at particular angles by controlling the incidence angle of the laser beam.

The technique of using laser pulses to affect surfaces is known. Typically, the use of lasers falls into two categories, one where the laser is used on a macro scale to perform cutting or large scale surface removal on metals or plastics, and the second where the lasers are used to affect the surfaces on a smaller scale. The latter technique involves using a relatively focused laser beam to create surface morphologies by melt flow or shock waves, i.e., the beam melts the surface of the material to create craters by movement of the liquid. Only a small number of pulses can be utilized on a given spot and the technique does not produce periodic or semi-periodic structures.

It is an object of this invention to provide a novel and unique method for increasing the surface area of metal, ceramic and composite materials though the use of multiple laser pulses, the surface morphology being affected on a micro scale by the creation of surface morphological structures on the magnitude of from ¼ to several hundred microns. The surface area of a treated metal, ceramic or composite is increased by up to a factor of 100 and the strength of the material is unaffected by the methodology.

It is a further object to provide such a method suitable for any metal, ceramic or composite and where the magnitude of the micro-roughness is controllable by varying parameters of the laser, such as number and duration of pulses, wavelength, energy density, angle of incidence and treatment environment, which in turn are dependent on the particular metal, ceramic or composite being treated.

It is a further object to provide novel metal, ceramic or composite surfaces of increased surface roughness produced by the method described above, the surfaces having periodic or semi-periodic morphological structures on the magnitude of from ¼ to several hundred microns.

SUMMARY OF THE INVENTION

The method for increasing surface area on a metal, ceramic or composite (ceramic-ceramic, metal-metal, ceramic-metal, ceramic-polymer and metal-polymer) comprises irradiating the surface with multiple laser pulses within certain parameters. Material removal at the surface of the metal, ceramic or ceramic composite occurs to a depth of up to 200 microns in a non-uniform manner, resulting in the formation of periodic or semi-periodic morphological structures on a scale of from ¼ to several hundred microns. The surfaces produced by this method comprise structures in the form of cones, columns, peaks, fingers, grooves and valleys, probably due to preferential absorption of the laser beam. The beam is scanned to induce change over as much of the surface as desired. The process can be performed in air at ambient pressure, under selected gases or at vacuum for the ceramic and composite materials, or under low pressure or at vacuum for metal surfaces.

The wavelength of the laser can be from UV to infrared. The beam is relatively unfocused, with an energy density of from 0.01 to 15 J/cm$^2$. A large number of pulses are utilized, with 50 pulses being a minimum and at least 200 pulses being preferred, and the pulses have a duration of from 1 picosecond to 1 millisecond. The particular values utilized are dependent on the particular material being treated, with characteristics of reflectivity, thermal absorption, thermal conductivity, density and specific heat being taken into account. In general, the shorter the pulse duration, the lower the necessary energy density. This methodology produces an increase in microroughness and surface area of up to two orders of magnitude.

BRIEF DESCRIPTION OF THE ILLUSTRATIONS

DETAILED DESCRIPTION OF THE INVENTION

The surface area of metals, ceramics and composites (ceramic-ceramic, ceramic-metal, metal-metal, ceramic-polymer and metal-polymer) is increased by creating periodic or semi-periodic micro-scale morphological structures on the surface of the material through the use of relatively unfocused multiple laser pulses. The material surface is altered to a maximum depth of 200 microns, such that the bulk properties of the material are not affected by the technique. Surface roughness and surface area can be increased by up to a factor of 100.

No specific pre-treatment is required for the material to be irradiated by this technique. Masking is not necessary, as it is desirable to shape all the exposed surface to increase surface area. Ceramic and ceramic composite materials can be irradiated at ambient temperature and pressure, in normal atmosphere. The technique can also be employed with ceramic and ceramic composites in controlled atmosphere situations, such as with the use of reactive or non-reactive gases. For metal surfaces, the irradiation must occur under vacuum or at low pressure (less than 760 torr) to prevent melt flow behavior and shock wave effects. Shock wave effects can also be reduced on metals by performing the technique in light gas atmospheres, such as hydrogen or helium.

Standard lasers capable of producing beams within the prescribed parameters can be employed. In the examples given later, a Questek V-beta Series 2000 laser was used. The laser wavelength can be varied by the use of different rare gas/halide gas combinations (e.g., 193 nanometers using ArF gas, 248 nanometers using KrF gas or 308 nanometers using XeCl gas), and in the examples the 248 nanometer wavelength was employed. Suitable wavelengths range from ultraviolet to infrared, and beam energy densities ranging from 0.01 to 15 J/cm$^2$ are utilized depending on the particular material. The laser must be able to be rapidly pulsed, preferably with durations of from 1 picosecond to 1 millisecond, with the preferred pulse duration being from 15 to 25 nanoseconds. Pulse repetition rates from 0.01 to 1000 Hz may be utilized.

The particular energy density and duration is variable and is dependent on the particular material being treated and the extent of surface roughness desired. Additionally, surface morphology can be controlled by these factors as well as by the angle of incidence of the beam.

The key step in the method is the use of a high number of low energy laser pulses to affect a given area. At least 50 pulses, and preferably at least 200 pulses, are irradiated on a single area, with the beam energy being less than 15 J/cm$^2$, and preferably from 2 to 8 J/cm$^2$ and even more preferably less than 4 J/cm$^2$. This minimum number of pulses is much higher and this maximum beam energy is much lower than is typically used in laser treatment of surfaces. As many as 100,000 pulses or more can be used on a single area. The laser may be scanned over the material surface to produce increased roughness and surface area over a large range.

The method comprises irradiating the surface of ceramics, metals or composites (ceramic-ceramic, ceramic-metal, metal-metal, ceramic-polymer or metal-polymer) with at least 50 pulses of a laser beam in the UV to infrared wavelength range having an energy density of between 0.01 to 15 J/cm$^2$, and most preferably from 2 to 4 J/cm$^2$, with pulse durations of from 1 picosecond to 1 millisecond. Surfaces containing metal must be irradiated in vacuum or with light gases to prevent melt flow and shock wave effects. Selective absorption of the beam results in the formation of semi-periodic surface structures having magnitudes of less than 200 microns, resulting in dramatically increased surface area without affecting the bulk properties of the material.

The following examples illustrate the method described above. Increase in surface roughness or area was determined by microscopic evaluation and model calculations. A periodic groove height "h", a periodic groove width "a", and a periodic groove spacing "b", with the features symmetrical in both directions gives the formula $A_m/A_o=[(2h/(a+b))+1]^2$, where $A_m$ is the new modified surface area and $A_o$ is the original surface area.

EXAMPLE 1

Referring to FIGS. 1 through 6, surface modification of an hydroxyapatite sample (Ca$_{10}$ (PO$_4$)$_6$(OH)$_2$)is shown. Hydroxyapatite is the main mineral for natural bone and shows a very desirable response among bio-active materials used for implants. The figures show successive stages of modification of this sample. The samples were processed in air, with a beam incidence normal to the sample surface.

Figure 1:
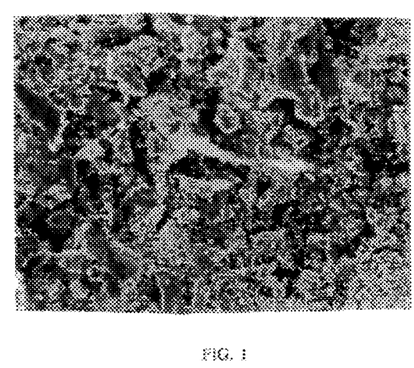
FIGS. 1 through 4 are scanning electron microscope (SEM) images of an hydroxyapatite sample.
Figure 2:
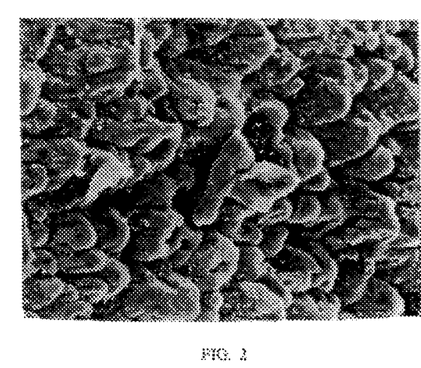
Figure 3:
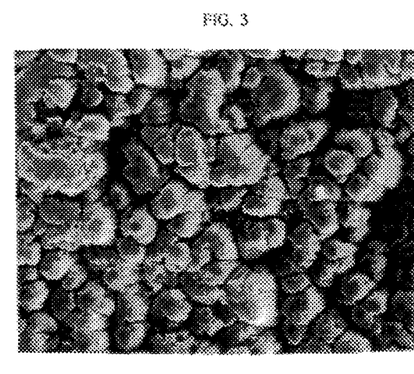
Figure 4:
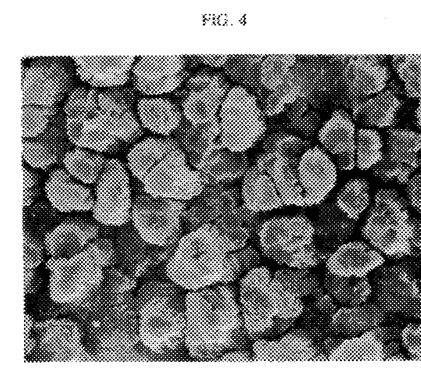

FIG. 1 is an SEM photograph of the untreated sample as received, at magnification of 500. FIG. 2 is the sample after treatment with 300 pulses, 20 nanosecond duration, at 2.0 to 2.5 J/cm$^2$, at magnification of 500. FIG. 3 is the sample after treatment with 300 pulses, 20 nanosecond duration, at 2.5 to 3.0 J/cm$^2$, seen at a magnification of 400. FIG. 4 is the sample after treatment with 600 pulses, 20 nanosecond duration, at 2.5 to 3.0 J/cm$^2$, at a magnification of 250. All samples were treated at 248 nanometer wavelength. As can be observed, periodic morphological structures are present in FIGS. 2, 3 and

EXAMPLE 2

Figure 5:
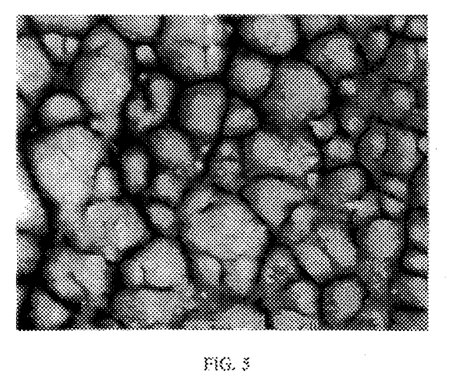
FIG. 5 is an SEM image of a silicon nitride sample.

FIG. 5 shows a silicon nitride sample processed in air with 1500 pulses, 20 nanosecond duration, at 3.5 to 4.0 J/cm$^2$ at 248 nanometer wavelength, beam incidence normal to the sample surface, at a magnification of 900. Semi-periodic peaks and valleys are observable.

EXAMPLE 3

Figure 6:
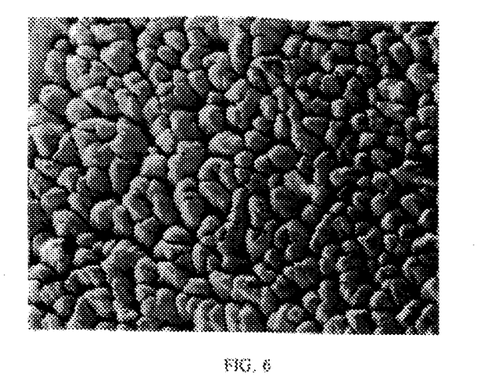
FIG. 6 is an SEM image of an alumina sample.

FIG. 6 is an alumina (Al$_2$O$_3$) sample treated in air at 4.0 J/cm$^2$ at 248 nanometer wavelength, beam incidence normal to the sample surface, at a magnification of 900. The flat section at the corner of the photograph shows the smooth surface morphology of the untreated sample surface. The remainder of the photograph shows the greatly increased surface area resulting from the semi-periodic structures created by the method.

EXAMPLE 4

Figure 7:
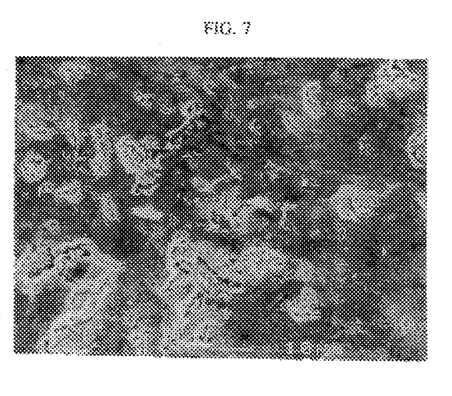
FIGS. 7 and 8 are SEM images of a YBa$_2$Cu$_3$O$_7$ semiconductor sample.
Figure 8:
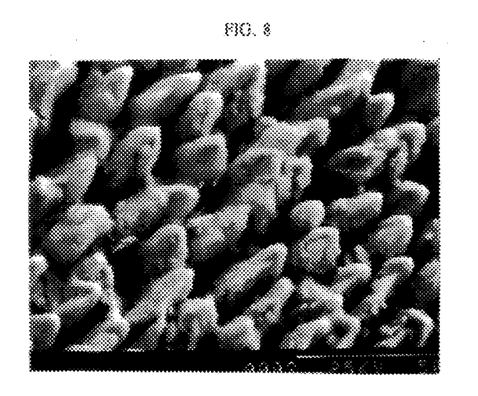

FIG. 7 is an untreated $YBa_2Cu_3O_7$ semiconductor sample at a magnification of 1000 showing the relatively smooth surface. FIG. 8 is a $YBa_2Cu_3O_7$ semiconductor sample irradiated in vacuum with 1000 pulses, 20 nanosecond duration, at 2.0 $J/cm^2$ at 248 nanometer wavelength, at a magnification of 400. The laser beam was impinged on the surface at an angle of 45 degrees. The semi-periodic structures formed on the surface are conical and are oriented 45 degrees in the direction of the laser beam.

EXAMPLE 5

Figure 9:
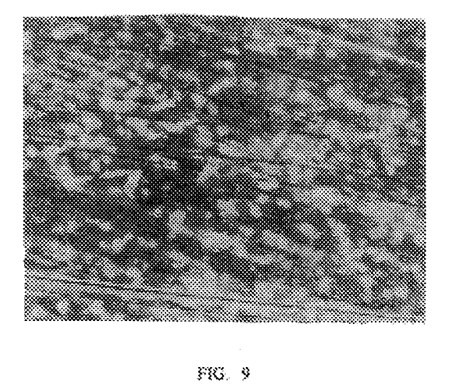
FIGS. 9 through 11 are SEM images of an SiC whisker reinforced alumina sample.
Figure 10:
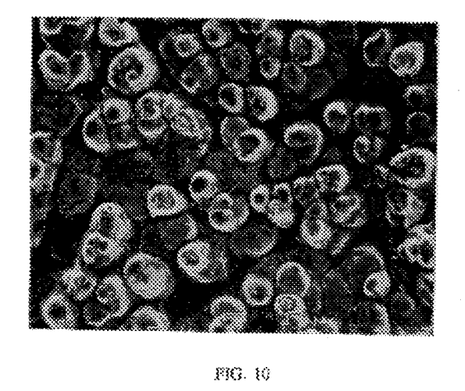
Figure 11:
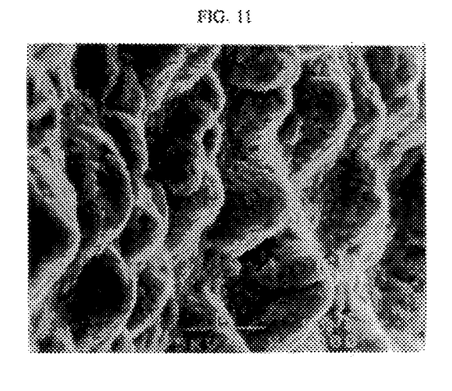

FIG. 9 shows the smooth surface of an untreated SiC whisker reinforced alumina sample. FIGS. 10 and 11 show the SiC whisker reinforced alumina sample as treated with 1200 pulses, 20 nanosecond duration, at 4.0 $J/cm^2$ at 248 nanometer wavelength, beam incidence normal to the sample surface. The surface was coated with a thin film of diamond by chemical vapor deposition. FIG. 10 is seen at an angle normal to the surface at a magnification of 500. FIG. 11 is a photograph taken at an angle of 60 degrees to the surface at a magnification of 2000. After deconvoluting for the tilt effects, the depth of the conical surface structures is calculated to be 20 to 30 microns.

EXAMPLE 6

Figure 12:
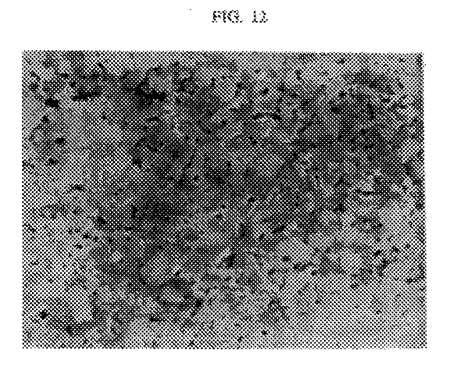
FIGS. 12 through 16 are SEM images of a tungsten carbide and cobalt composite sample.
Figure 13:
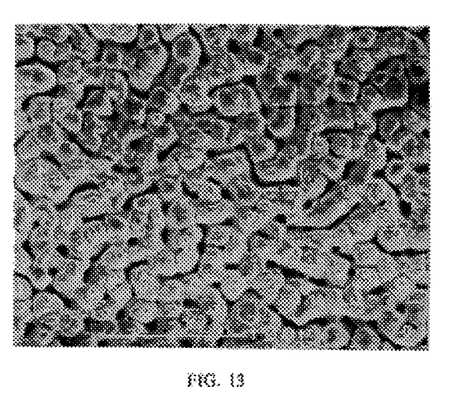
Figure 14:
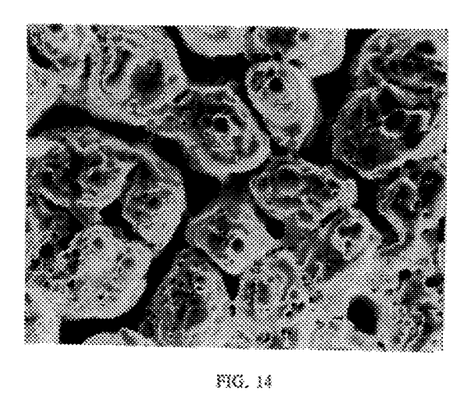
Figure 15:
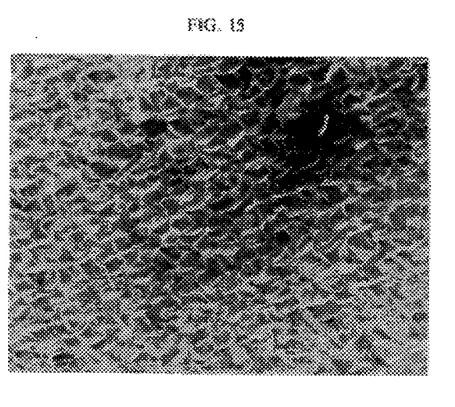
Figure 16:
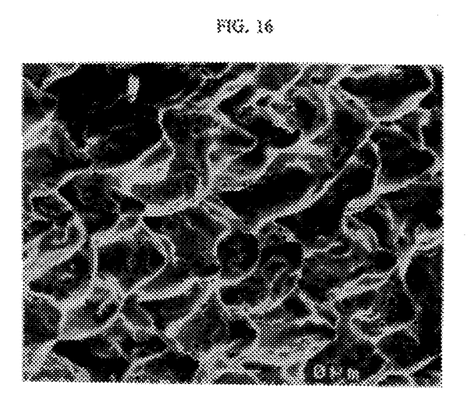

FIGS. 12 shows an untreated tungsten carbide/cobalt composite sample (10 Co/90 WC) at magnification of 2500. FIGS. 13 through 16 show the sample after treatment with 1000 pulses, 20 nanosecond duration, at 3.0 $J/cm^2$, beam incidence normal to the sample surface. FIGS. 13 and 14 are taken normal to the surface, at magnifications of 270 and 1000, respectively. FIGS. 15 and 16 are taken at an angle of 60 degrees to the surface. Calculations from these figures show that the stalagmitic structures have a height of approximately 20 microns and a periodicity of approximately 10 to 20 microns. Calculations on these values indicate that the surface area has been increased by 2.25 to 25 times the original surface area.

EXAMPLE 7

Figure 17:
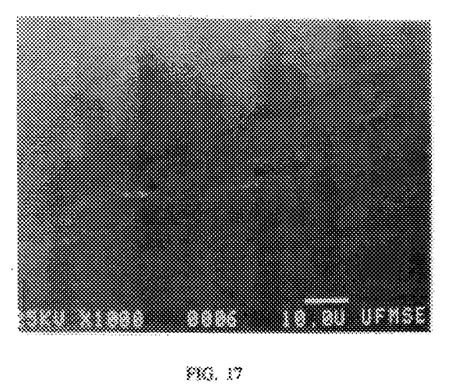
FIGS. 17 and 18 are SEM images of a silicon sample.
Figure 18:
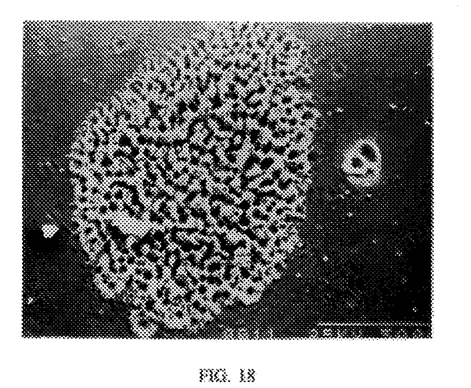

FIG. 17 shows an untreated silicon sample at magnification of 1000. FIG. 18 shows the silicon sample processed in vacuum with 250 laser pulses, 20 nanosecond duration, at 6.0 to 8.0 $J/cm^2$, beam incidence normal to the sample surface, at a magnification of 60. This figure shows that a high degree of surface roughness can be achieved in covalently bonded samples, the vacuum acting to eliminate the detrimental effects of shock waves on metal surfaces.

EXAMPLE 8

Figure 19:
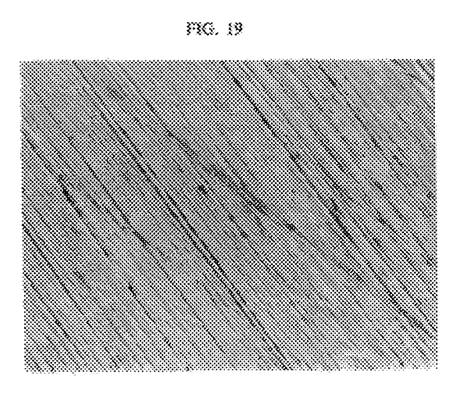
FIGS. 19 through 21 are SEM images of a 304 stainless steel sample.
Figure 20:
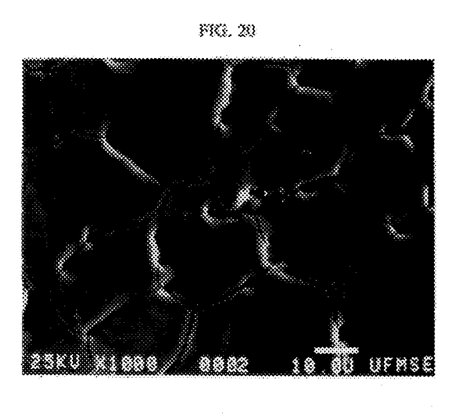

FIG. 19 shows the relatively smooth surface of a 304 stainless steel sample at magnification of 500. FIG. 20 shows the 304 stainless steel sample processed in air at ambient pressure with 100 pulses, 20 nanosecond duration, at 3.5 to 4.0 $J/cm^2$, beam incidence at 45 degrees to the sample surface, at 1000 magnification. Note that no surface morphological structures have been created sue to melt flow.

Figure 21:
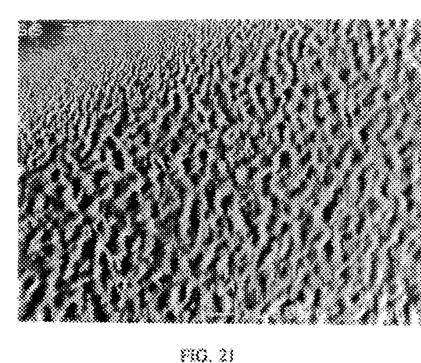
Figure 22:
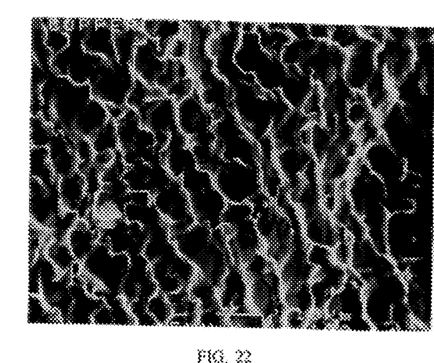
FIG. 22 is an SEM image of a copper sample.

FIG. 21 shows a 304 stainless steel sample processed in vacuum (less than 1 torr) with 100 pulses, 20 nanosecond duration, at 3.5 to 4.0 $J/cm^2$, beam incidence at 45 degrees to the sample surface at 80 magnification. Under these conditions, semi-periodic surface morphologies on a micro scale are produced.

EXAMPLE 9

FIG. 19 shows a copper sample processed in vacuum (less than 1 torr) with 100 pulses, 20 nanosecond duration, at 3.5 to 4.0 $J/cm^2$, irradiated at a 45 degree angle to the sample surface, and shown at 1100 magnification. Even though some melt flow characteristics are observable, the creation of semi-periodic structures over a large surface area is clearly illustrated.

EXAMPLE 10

Figure 23:
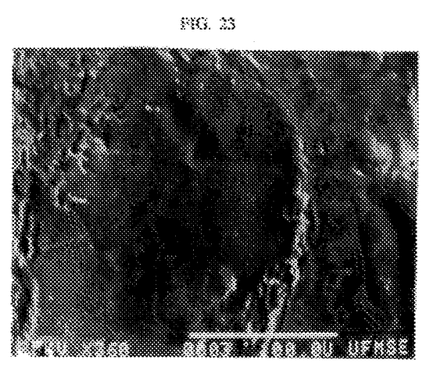
FIGS. 23 and 24 are SEM images of a nickel superalloy sample.

FIG. 23 shows a nickel superalloy sample processed in air with 100 pulses, 20 nanosecond duration, at 3.5 to 4.0 $J/cm^2$, irradiated at a 45 degree angle and at magnification of 360. Note that no surface structures have been created.

Figure 24:
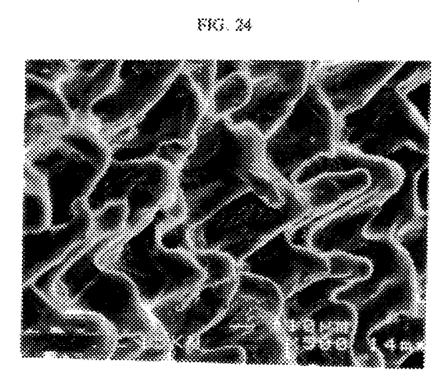

FIG. 24 shows a nickel superalloy sample identical to the sample in FIG. 20, processed in vacuum (less than 1 torr) with 100 pulses, 20 nanosecond duration, at 3.5 to 4.0 $J/cm^2$, irradiated at a 45 degree angle and at magnification of 500. Here periodic surface morphologies have been created.

EXAMPLE 11

Figure 25:
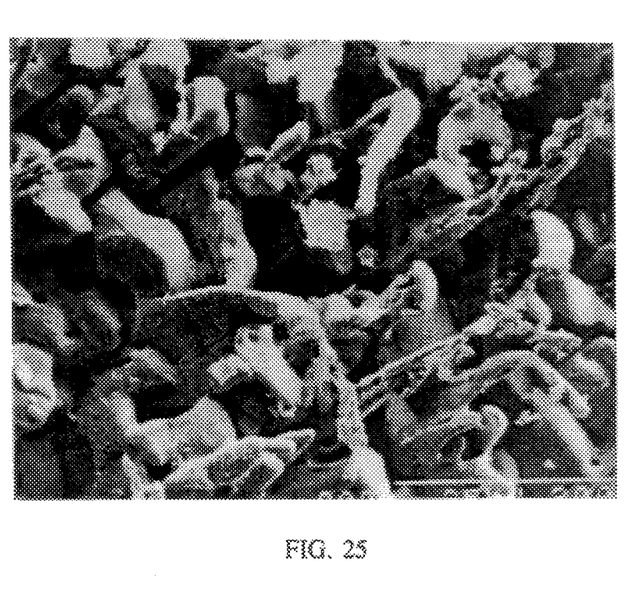
FIG. 25 is an SEM image of a Ni$_3$Al sample.

FIG. 25 shows a $Ni_3Al$ sample processed in vacuum (approximately $10^{-4}$ torr) with 500 pulses, 20 nanosecond duration, at 3.5 to 4.0 $J/cm^2$, irradiated at a 45 degree angle relative to the sample surface, at magnification of 400, showing the presence of semi-periodic morphological structures.

We claim:

1. A surface on a metal material having periodic conical surface structures less than 200 microns in height and less than 100 microns in thickness.

2. The surface of claim 1, further comprising valleys less than 300 microns in width between said conical surface structures.

3. The surface of claim 1, where said surface is produced by steps comprising:

(A) providing a laser for producing a beam of radiation having a wavelength within the UV to infrared range, an energy density within the range of 0.01 to 15 $J/cm^2$, and pulse durations within the range of 1 picosecond to 1 millisecond;

(B) irradiating the surface of the material to be treated with at least 50 pulses of radiation from said laser, said radiation having an energy density of between 0.01 to 15 $J/cm^2$, said pulses having duration of between 1 picosecond to 1 millisecond, at a pressure of less than 760 torr.

4. The surface of claim 3, further comprising valleys less than 300 microns in width between said conical surface structures.

5. A surface on a ceramic material having periodic conical surface structures less than 200 microns in height and less than 100 microns in thickness.

6. The surface of claim 5, further comprising valleys less than 300 microns in width between said conical surface structures.

7. The surface of claim 5, where said surface is produced by steps comprising:

(A) providing a laser for producing a beam of radiation having a wavelength within the UV to infrared range, an energy density within the range of 0.01 to 15 $J/cm^2$, and pulse durations within the range of 1 picosecond to 1 millisecond;

(B) irradiating the surface of the material to be treated with at least 50 pulses of radiation from said laser, said radiation having an energy density of between 0.01 to 15 J/cm$^2$, said pulses having duration of between 1 picosecond to 1 millisecond.

8. The surface of claim 7, further comprising valleys less than 300 microns in width between said conical surface structures.

9. A surface on a composite material containing metal or ceramic having periodic conical surface structures less than 200 microns in height and less than 100 microns in thickness.

10. The surface of claim 9, further comprising valleys less than 300 microns in width between said conical surface structures.

11. The surface of claim 9, where said surface is produced by steps comprising:

(A) providing a laser for producing a beam of radiation having a wavelength within the UV to infrared range, an energy density within the range of 0.01 to 15 J/cm$^2$, and pulse durations within the range of 1 picosecond to 1 millisecond;

(B) irradiating the surface of the material to be treated with at least 50 pulses of radiation from said laser, said radiation having an energy density of between 0.01 to 15 J/cm$^2$, said pulses having duration of between 1 picosecond to 1 millisecond.

12. The surface of claim 11, further comprising valleys less than 300 microns in width between said conical surface structures.

* * * * *